US008520801B2

(12) United States Patent  (10) Patent No.: US 8,520,801 B2
Henning  (45) Date of Patent: Aug. 27, 2013

(54) MOBILE X-RAY UNIT

(75) Inventor: Johan Henning, Veenendaal (NL)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 13/335,414

(22) Filed: Dec. 22, 2011

(65) Prior Publication Data

US 2012/0163538 A1 Jun. 28, 2012

Related U.S. Application Data

(60) Provisional application No. 61/426,878, filed on Dec. 23, 2010.

(30) Foreign Application Priority Data

Dec. 22, 2010 (NL) ...................................... 2005903

(51) Int. Cl.
*A61N 5/10* (2006.01)
(52) U.S. Cl.
USPC .......................................................... 378/65
(58) Field of Classification Search
USPC .......................................................... 378/65
See application file for complete search history.

(56) References Cited

U.S. PATENT DOCUMENTS

| 4,675,890 | A  | * | 6/1987 | Plessis et al. | ................. | 378/121 |
| 2003/0048875 | A1 | | 3/2003 | Mihara et al. | | |
| 2007/0076851 | A1 | | 4/2007 | Pellegrino | | |
| 2010/0246766 | A1 | * | 9/2010 | Kindlein et al. | ................. | 378/65 |
| 2012/0039444 | A1 | * | 2/2012 | Baic et al. | ..................... | 378/147 |

FOREIGN PATENT DOCUMENTS

| EP | 2005992 A1 | 12/2008 |
| WO | WO2008/118198 A1 | 10/2008 |

OTHER PUBLICATIONS

Topex, Inc., "SRT 100 Superficial Radiotherapy System for the Treatment of Skin Cancer," http://www.harpell.ca/wp-content/uploads/2009/11/topexbrochure_v10.pdf., (2007), (6 pages).*
Search Report and Written Opinion in related Netherlands Application No. 2005903 dated May 28, 2011 (8 pages).
Topex, Inc., "Regulatory Information," http://www.tpoexmedical.com/product2.html, 2007 (1 page).

* cited by examiner

*Primary Examiner* — Glen Kao
(74) *Attorney, Agent, or Firm* — Finnegan, Henderson, Farabow, Garrett & Dunner LLP

(57) ABSTRACT

One embodiment of the present disclosure is directed to a mobile X-ray unit. The mobile X-ray unit may include a base for accommodating a control unit, a power supply, and a cooler. The mobile X-ray unit further including an articulated arm associated with the base and coupled to an X-ray applicator. The X-ray applicator including an X-ray tube having an anode for generating an acceleration field and a target element for generating an X-ray beam, wherein a longitudinal axis of the anode is substantially parallel to a longitudinal axis of the X-ray tube.

16 Claims, 11 Drawing Sheets

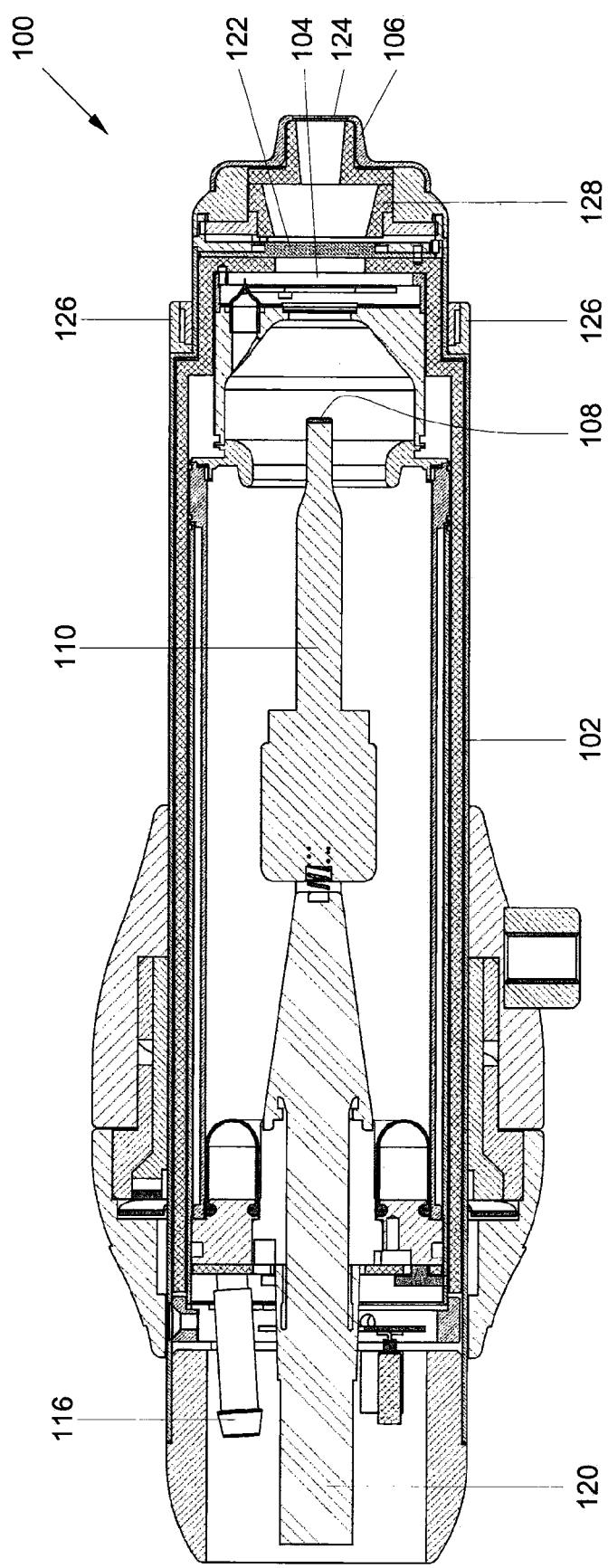
Fig. 7, E-E

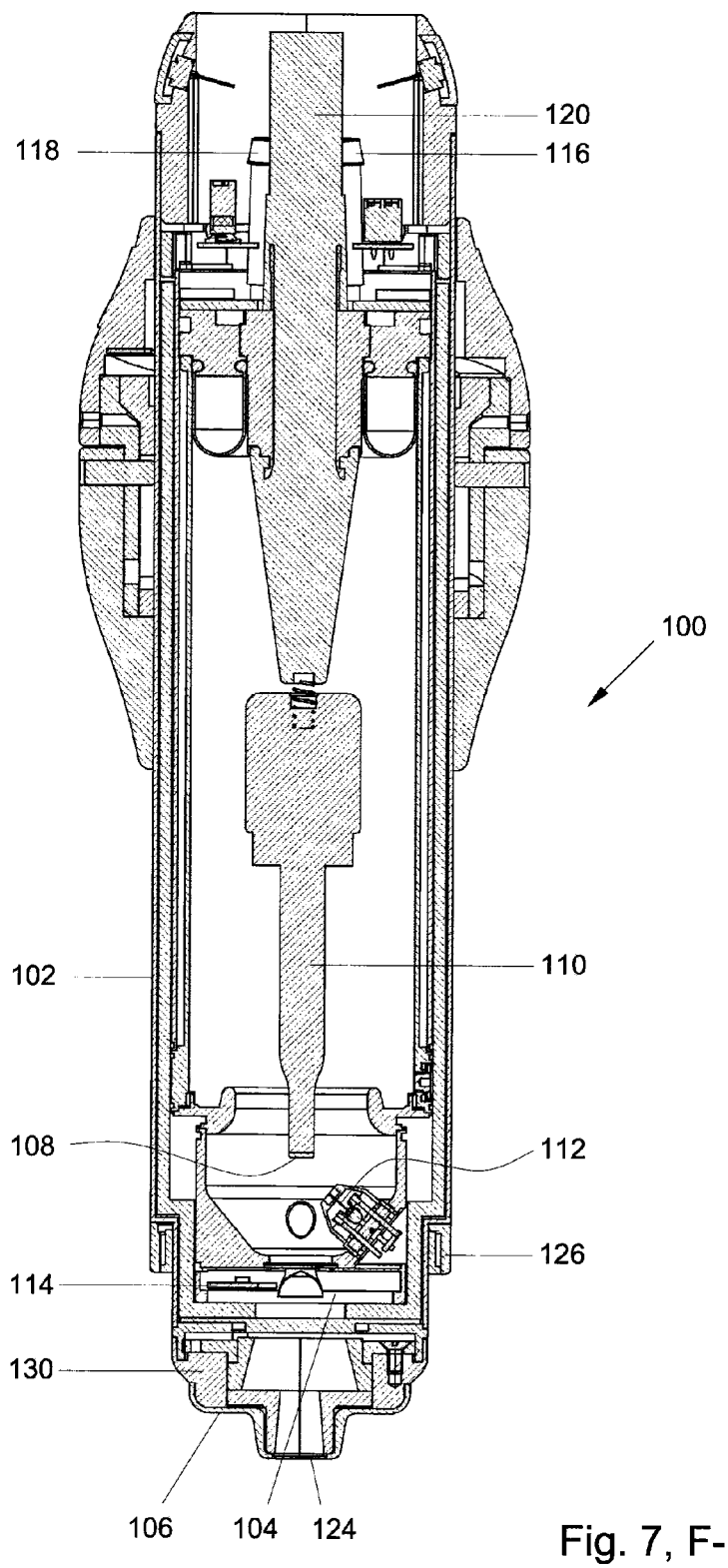
Fig. 7, F-F

MOBILE X-RAY UNIT

CROSS-REFERENCE TO RELATED APPLICATIONS

This application claims the benefit of priority based on U.S. Provisional Patent Application No. 61/426,878, filed Dec. 23, 2010, and Netherlands Patent Application No. 2005903, filed Dec. 22, 2010, which are all incorporated herein by reference.

FIELD OF THE INVENTION

The present disclosure relates generally to a mobile X-ray unit. The present disclosure further relates to a method of manufacturing the X-ray unit and a method of delivering an X-ray beam.

BACKGROUND OF THE INVENTION

The incidence rate of skin cancer has substantially increased in the last decade of the 20$^{th}$ century. It is appreciated that over 1.3 million new skin cancers are diagnosed annually, which is increasing at a rate of about 5% per year. Increased exposure to the sun without skin protection and a decreased ozone layer are regarded as the main causes of this increase—a problem estimated to be costing over 1 billion Euros in annual medical treatment expenses. Over 80% of skin cancers occur in the head and neck regions with 50% occurring in patients over 60 years of age. It is expected that a portion of the senior population will double in year 2025 compared to the present demographics. Because of the growing incidence of skin cancer and increasing share of the senior population in the overall demographics, much focus has been placed on cancer treatments and cancer treatment logistics.

Non-proliferative cancers, which are defined by substantially superficial lesions, may be treated in different ways. In one example, non-proliferative cancers may be treated surgically. Surgery, may, however, have certain drawbacks, such as, for example, long waiting lists, complications related to post-treatment care, and risk of infection. Alternatively, patients may undergo irradiation using electrons of soft X-rays. Irradiation may have an advantage of being non-invasive and of a short duration (a treatment session may be as short as 2 to 4 minutes). It will be appreciated that usually the integral treatments using radiotherapeutic techniques may require a number of sessions.

Recently, the use of a mobile and portable X-ray unit has been suggested, which may be used inside a hospital radiotherapy department. An embodiment of such portable unit is described in US 2007/0076851. It will be appreciated that the terms 'mobile' and 'portable' in the context of the present application may be interchanged as these terms equally relate to an easily moved or transported device, for example, a device which may be moved or transported by a single individual.

Existing X-ray units include an X-ray source and a filtering device having a plurality of filters rotatably arranged with respect to a focal point of the X-ray tube for changing filtering characteristics on demand. The plurality of filters are arranged in a filtering device, which is transversely arranged with respect to a longitudinal axis of the X-ray tube. These mobile X-ray units, while effective, may have certain drawbacks. For example, X-ray beam characteristics may be affected by the internal geometry of the X-ray tube, leading to, for example, a broadened penumbra of the X-ray beam. Furthermore, the overall dimension of the X-ray tube may be relatively large. In particular, the existing X-ray tubes may have an enlarged size and an irregular shape due to the filter carousel. The irregular shape may shift the center of gravity of the existing X-ray tubes off-center, which may make it more difficult to stabilize the existing X-ray tube in a treatment position.

SUMMARY OF THE INVENTION

It is an object of the present disclosure to provide a mobile X-ray unit having improved operational characteristics. In particular, it is an object of the present disclosure to provide a mobile X-ray unit having improved penumbra of the X-ray beam and/or a reduced skin dose when dose delivery is specified at 5 mm depth. It is a further object of the invention to provide an improved X-ray unit where an X-ray tube may be easily stabilized for assuming a treatment position. To this end, in the mobile X-ray unit, according to the present disclosure, a longitudinal axis of an anode may be disposed substantially parallel to a longitudinal axis of the X-ray tube.

It will be appreciated that in general the anode may have a substantially cylindrical shape.

In one embodiment, the X-ray applicator may include a longitudinal axis, the longitudinal axis of the X-ray tube may be substantially parallel to a longitudinal axis of the X-ray applicator.

In various embodiments, the longitudinal axis of the anode, the longitudinal axis of the X-ray tube, and the longitudinal axis of the X-ray applicator may be co-axially disposed. In this arrangement, an X-ray beam may be generated which propagates along the longitudinal axis of the X-ray applicator. Accordingly, a sharpened penumbra may be achieved by aligning a collimator with respect to the X-ray beam. In addition, the arrangement may simplify the construction of the X-ray tube which may decrease the overall weight of the X-ray applicator.

In addition, for skin irradiation applications, the X-ray applicator may be located vertically or with a small inclination with respect to a vertical axis. Accordingly, by arranging the body of the anode parallel to the longitudinal axis of the X-ray applicator the mechanical balance of the X-ray applicator in use will may be improved.

In various embodiments, the X-ray tube may have an exit window for emitting the X-rays generated at the target, the X-ray tube may further include a collimator for shaping the generated X-ray beam. The target, the exit window, and the collimator may be arranged to be substantially on the longitudinal axis of the X-ray tube in a spaced apart configuration.

It will be appreciated that the target, the collimator, and the exit window may be mounted at different locations in the X-ray tube. It will be further appreciated that the target may be provided on an outer surface of the anode, substantially perpendicular to the longitudinal axis of the anode.

When the target element, the collimator, and the exit window on the longitudinal axis of the X-ray tube are arranged in a spaced apart configuration, the centre of gravity of the X-ray tube assembly may be located on or close to the longitudinal axis of the X-ray tube. Accordingly, the X-ray tube may be easily positioned in space so that no oblique forces may act on the centre of gravity. In some embodiments, the X-ray tube may have a rotational symmetry, at least with respect to components having a substantial weight.

Furthermore, by providing the X-ray tube with an exit window and by allowing the X-ray beam to propagate substantially parallel to the longitudinal axis of the X-ray tube, beam characteristics of the X-ray tube may be improved. In particular, it may be possible to generate an X-ray beam having a sharpened penumbra.

In addition, the X-ray tube configuration may be advantageous from a mechanical perspective since balancing of the X-ray tube on the articulated arm may be simplified. It will be appreciated that the X-ray tube, accommodated in the outer housing, represents a relatively slim (outer diameter of less than 10 cm) elongated cylinder (length of about 30 cm), which may be displaced in a vertical direction for delivering the X-ray beam to the patient. Once the internal geometry of the X-ray tube is co-axial, having the centre of gravity located on or close to the longitudinal axis of the X-ray tube permits the weight of the X-ray tube to be suitably balanced so as to permit easy and reproducible displacement of the articulated arm supporting the X-ray applicator. Also positioning the X-ray tube at small oblique angles may be simplified because of the relatively smaller oblique forces acting on the centre of gravity.

In various embodiments, a distance between the target element and the collimator is in the range between 4 and 10 cm, and preferably between 5 and 6 cm. It is found that by setting a distance between the X-ray target element and the collimator in the range of 4 to 10 cm, and preferably to a distance of about 5 to 6 cm, a still further improvement of the beam characteristics may be achieved. For example, it is found that an improved beam flatness as well as sharpened penumbra are achievable for the target element-collimator distance of 4 to 10 cm, and particularly for the target element-collimator distance of about 5 to 6 cm, due to a relative small focal size. For example, for the target element-collimator distance of about 5 cm penumbra of 1.5-1.8 mm may be achievable (specified for 20/80% lines). It will be appreciated that the overall length of the X-ray applicator may be between 10 and 30 cm, and the X-ray applicator may be adapted to perform irradiation with the applicator substantially in contact with or close to the skin. The present arrangement of relatively small distances from the target element to the collimator and the exit window, may reduce the amount of scattered radiation, thereby sharpening the penumbra. It is appreciated that a sharpened penumbra may be important particularly for treating of small lesions, such as skin cancers so as to protect healthy tissue. In some embodiments, the distance between the collimator and the exit window may be minimized.

In various embodiments, the collimator may be provided with automatic identification devices configured to generate a signal in the control unit representative of collimator characteristics.

It may be advantageous to automatically identify when the collimator has been inserted in the X-ray tube so as to minimize or eliminate human errors in defining the field geometry. For example, the collimator may be positioned in a receptacle having a resistive path whose resistivity may be changed. The collimator may be arranged with projections adapted to cooperate with the resistive path of the receptacle for changing the resistivity of the receptacle, and thus, generating a signal indicating that the collimator has been inserted into the receptacle. In some embodiments, the signal may be made available to the control unit of the mobile X-ray unit for independent verification. It is contemplated that the mobile X-ray unit includes a set of collimators each having identification devices.

In an alternative embodiment, a part of the X-ray unit may include a plurality of contacting pins configured to be connected to the collimator. Each of the different types of collimator may be provided with at least one contacting pad located in a uniquely defined position such that when the collimator contacts one of the contact pins on the X-ray unit the collimator provides or completes an electrical circuit. The contacts may be positioned at different locations on each collimator so as to uniquely identify each collimator. When the collimator is connected to the X-ray unit, the contacts may complete a specific electric circuit. The control unit may detect the completion of each electric circuit and transmits a signal to the control unit to indicate which type of collimator is in place.

In yet another alternative embodiment, the collimator identification devices may include a magnetic, optical, RFID, or another arrangement. For example, a suitable bar code may be provided on the collimator which may be read-out prior to confirming the ready status of the device.

In various embodiments, the X-ray unit may include at least one signaling device configured to indicate the generation of an X-ray beam.

It may be advantageous to provide an indication that the X-ray beam is on. The signaling device may be a suitable light on the X-ray applicator. One or more light emitting diodes may be used for this purpose. It may be possible to provide a plurality of signaling devices with different signals depending upon the energy of the generated X-ray beam.

For example, for the X-ray beam of a lower portion of the spectrum (about 50 kV), a first indicator may be used, such as, for example, a first light color. For an intermediate portion of the spectrum (about 60-65 kV), a second indicator may be used, such as, for example, a second light color. Finally, for the higher portion of the spectrum (66-75 kV, preferably 66-70 kV), a third indicator may be used, such as, for example, a third light color. It will be appreciated that a plurality of possibilities exist for indicating different spectra, including but not limited to a progressive illumination of a plurality of indicators upon hardening of the delivered X-ray beam. It will be further appreciated that such indication of the kV range may be disposed in the device, in a user interface, or in a supplementary unit. It will be further appreciated that the named kV ranges may be scaled with, for example the factors 1:1; 1:2; 1:3; 1:4; 1:5. Preferably, the signaling devices comprise a light indicator arranged on an outer housing. The arrangement of the signaling devices is advantageous as the patient is made aware about the starting point and the termination of irradiation so that the patient may retain a static position during the course of treatment.

In various embodiments of the present disclosure, the mobile X-ray unit may include a cooler arranged with piping to provide a cooling medium in a vicinity of the X-ray tube. The piping may run in a space between the X-ray tube and a shielding wall associated with the X-ray tube.

It may be advantageous to provide a space between the outer surface of the X-ray tube and the inner surface of the X-ray tube, that is at least partially filled with a coolant. In some embodiments, it may be advantageous to provide circulated water as a cooling agent due to high specific heat capacity, offering improved heat transfer of water with respect to a gas. However, pressurized gas may also be used as a suitable coolant. In some embodiments, a temperature sensor may be arranged on the outer housing of the X-ray applicator for measuring actual temperature of the outer housing. The temperature sensor may be connected to the control unit for controlling the cooler and/or for controlling the high voltage supply. Should the temperature rise above a pre-determined shut-off value, the control unit may be arranged to disable the high voltage supply and/or to intensify the cooling mode, for example, by increasing a pumping capacity of the coolant.

In various embodiments of the present disclosure, a radiation detector may be provided inside the outer housing for detecting the X-ray beam.

It may be advantageous to provide an independent radiation detector for detecting the presence of the generated X-ray beam. In some embodiments, the mobile X-ray unit includes a primary timer which sets a time for the high voltage supply for delivering a predetermined radiation dose. The radiation sensor accommodated inside the outer housing of the X-ray applicator may be part of a secondary timer circuit adapted to shut down the high voltage supply after the predetermined radiation dose has been delivered. In this way radiation safety control may be improved.

In various embodiments, the X-ray applicator may include an exit surface configured to be oriented towards a patient. The surface may be covered by an applicator cap.

It may be advantageous to provide an applicator cap as it may have many functions in use. In a first example, the applicator cap may be used for protecting the exit surface of the X-ray applicator from intra-patient contamination. In another example, thickness of the cap in a direction of the beam propagation may be selected to be sufficient for substantially eliminating electron contamination from the X-ray beam. It will be appreciated that those skilled in the art will readily appreciate the relation between the energy of the secondary electrons emanating from the X-ray tube and a required thickness of a given material, for example plastic, glass, ceramics sufficient for fully intercepting these electrons. In some embodiments, the applicator cap may be disposable. In general, the thickness of the applicator cap in a region traversed by the useful X-ray beam may be between 0.3 and 3 cm.

In yet another example, the applicator cap may function as a heat absorber to dissipate the elevated temperature of the X-ray applicator. As a result the patient will feel the applicator contacting the skin as a slightly warm object.

In various embodiments, the X-ray applicator may be connected to the base by way of a flexible cable and displaceable panel. The flexible cable may be disposed in a displaceable panel.

It may be advantageous to provide an intermediate mechanical unit connecting the base of the mobile X-ray unit and the X-ray applicator for housing the flexible cables. This arrangement may prevent entanglement of the cables. The displaceable panel may be arranged with a pre-defined travel distance having a lowest achievable stand position and a highest achievable stand position. The pre-defined travel distance may be advantageous for increasing durability of the cables, tubes, and wiring of the mobile X-ray unit, especially of the tubes accommodating the coolant.

In various embodiments, the displaceable panel may include a user interface for controlling the X-ray unit. In some embodiments, the user interface includes a display. For example, the display may be implemented as a touch screen arranged for enabling data input. Alternatively, display may be arranged for echoing data. In this embodiment, buttons or other suitable input devices may be provided for entering input data into the X-ray unit.

Another embodiment of the present disclosure is directed to a method for manufacturing a mobile X-ray unit. The mobile X-ray unit may include a base for accommodating a control unit, a power supply, and a cooler. An articulated arm may be associated with the base and may support an X-ray applicator having an X-ray tube. The X-ray tube may have a longitudinal axis and may include an anode for generating an acceleration field and a target element for generating an X-ray beam. The method may include connecting the X-ray applicator to the base by a connector comprising a flexible cable; and arranging the X-ray tube so that the longitudinal axis of the anode is disposed substantially parallel to the longitudinal axis of the X-ray tube.

In some embodiments, the anode may include a target element for generating an X-ray beam. The X-ray tube may include an exit window and a collimator for shaping the generated X-ray beam at the target element. The method may further include the step of arranging the target element, the exit window, and the collimator to be substantially on the longitudinal axis of the X-ray tube in a spaced apart configuration.

In a particular embodiment, the target element, the collimator, and the exit window may be disposed substantially parallel to each other and may be arranged to extend substantially at right angles to the longitudinal axis of the X-ray tube.

In various embodiments, the target element and the collimator are accommodated in a substantially cylindrically shaped X-ray applicator. A direction of propagation of the generated X-ray beam may be substantially parallel to a longitudinal axis of the X-ray applicator. Further advantageous embodiment of the method according to the invention will be discussed with reference to FIG. 3.

Another embodiment of the disclosure may be directed to a method of delivering an X-ray beam for irradiating a superficial lesion using an X-ray unit. The mobile X-ray unit may include a base for accommodating a control unit, a power supply, and a cooler. An articulated arm may be associated with the base and support an X-ray applicator. The X-ray applicator may be connected to the base and including an X-ray tube. The X-ray tube may have a longitudinal axis and include an anode for generating an acceleration field and a target element for generating an X-ray beam. The longitudinal axis of the anode may be disposed substantially parallel to the longitudinal axis of the X-ray tube.

Another embodiment of the disclosure may be directed to an applicator cap for an X-ray unit including an X-ray tube accommodated in an X-ray applicator. The X-ray applicator may have an exit surface directed away from a base. The applicator cap may be configured to cover at least the exit surface. The applicator cap may be disposable. In some embodiments, a thickness of the cap in a direction of the beam propagation is sufficient for substantially eliminating electron contamination from the X-ray beam. An applicator cap may be advantageously manufactured from a substantially transparent material for enabling visualization of delineation between the exit surface of the X-ray applicator and a lesion to be treated.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 7, E-E presents a cross-section along line VII-E of the X-ray tube of FIG. 7, according to embodiments of the present disclosure.

FIG. 7, F-F presents a cross-section along line VII-F of the X-ray tube of FIG. 7, according to embodiments of the present disclosure.

DESCRIPTION OF THE EMBODIMENTS

Reference will now be made in detail to the present exemplary embodiments of the invention, examples of which are illustrated in the accompanying drawings. Wherever possible, the same reference numbers will be used throughout the drawings to refer to the same or like parts.

Figure 1B:
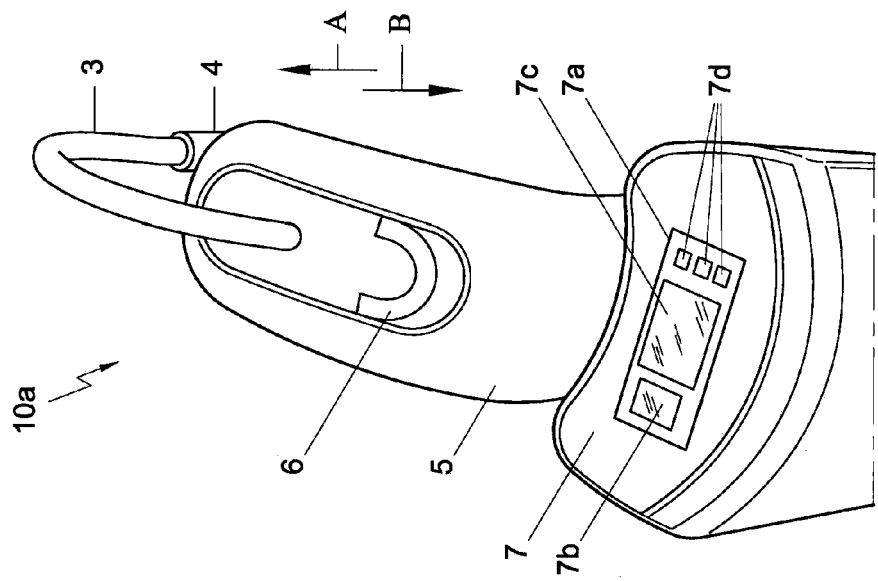
FIG. 1b presents a partial perspective view of the mobile X-ray unit illustrating displacement of an X-ray applicator of the mobile X-ray unit relative to a base of the mobile X-ray unit, according to embodiments of the present disclosure.
Figure 1A:
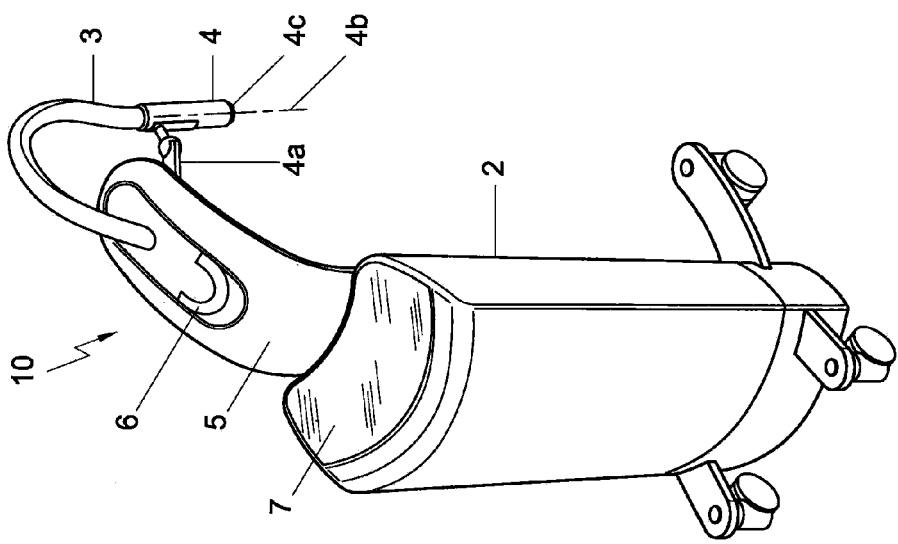
FIG. 1a presents a perspective view of a mobile X-ray unit, according to embodiments of the present disclosure.

FIG. 1a presents a perspective view of a mobile X-ray unit according to the present disclosure. The mobile X-ray unit 10 includes a base 2 having at least a high voltage supply unit, a cooling system, and a control unit (FIG. 2) for controlling an operation of an X-ray applicator 4. The X-ray applicator 4 includes an X-ray tube (FIG. 3) disposed in an outer housing of the X-ray applicator 4. The X-ray applicator 4 may be connected to the base 2 using flexible cables 3, which may be at least partially disposed in a displaceable panel 5. The X-ray applicator 4 may be coupled to an articulated arm 4a, which may include a pivot for varying the position of the X-ray applicator 4 in space. The applicator 4 may include a longitudinal axis 4b and an exit window 4c through which the generated X-ray beam may be emitted. The articulated arm 4a may also be connected to displaceable panel 5 for so as to alter of a vertical position of the applicator 4. In some embodiments, the displaceable panel 5 may be provided with a handle 6 enabling easy manipulation thereof. The displaceable panel 5 may be guided along suitable rails for enabling a substantially smooth and shock-free displacement thereof.

The base 2 may be provided with three or more wheels for enabling displacement of the X-ray unit to a different location. The wheels may be mounted using suitable bearings for enabling displacement of the X-ray unit. Preferably, the wheels may be interconnected by a deformable frame which may ensures that all wheels make contact with an underlying surface, such as a floor or ground, even if such surface is not completely flat.

In an exemplary embodiment, the X-ray applicator 4 and the X-ray tube (shown in FIG. 3) may be disposed co-axially. A target element, a collimator, and an exit window of the X-ray tube may be in parallel. The exit window, the target element, and the collimator may extend substantially perpendicularly to a longitudinal axis 4b of the X-ray tube. In some embodiments, the X-ray tube may have a rotational symmetry with respect to the target element, the collimator, suitable filters, and the exit window. In particular, the center of gravity of the X-ray tube may be provided on the longitudinal axis 4b.

The displaceable panel 5 may include a display 7, which may function as a suitable user interface 7a. For example, patient data, such as, for example, a photo of the patient and/or a photo of a lesion, may be provided in window 7b, whereby relevant patient information, such as the date of birth, gender, dose prescription, and dose delivery protocol may be displayed in window 7c. Inputs 7d may also be provided. Additionally and/or alternatively, suitable hardware switches or buttons may be provided. The display panel 7 may also include a button, switch, or other input device to activate an indicator (e.g., a light source). Alternatively, the light source 8c may always be on when the X-ray unit is switched on.

FIG. 1b presents a partial perspective view of the mobile X-ray unit illustrating movement of the displaceable panel. In this enlarged view 10a, specific elements of the displaceable panel 5 are depicted. A handle 6 may be implemented as a mechanical item for pulling or pushing the displaceable panel 5. Alternatively, the handle 6 may be arranged as an electrical actuator for triggering motors (not shown) for displacing the displaceable panel 5. For example, when the handle 6 is pulled the motors may be activated for causing the panel 5 to displace in a direction A. Pushing of the handle 6 may cause lowering of the panel 5 in a direction B. In some embodiments, the mobile X-ray unit 10 includes stops, limits, or other known structures for limiting the movement of the displaceable panel 5. This may be advantageous for ensuring mechanical stability of the mobile X-ray unit 10 (limitation of the upper level) and may also be beneficial for preventing cable damage (limitation of the lower level). In some embodiments, the displaceable panel 5 may travel along built-in rails whose length may be chosen for limiting the displacement range of the panel 5 in a desirable way.

Figure 1C:
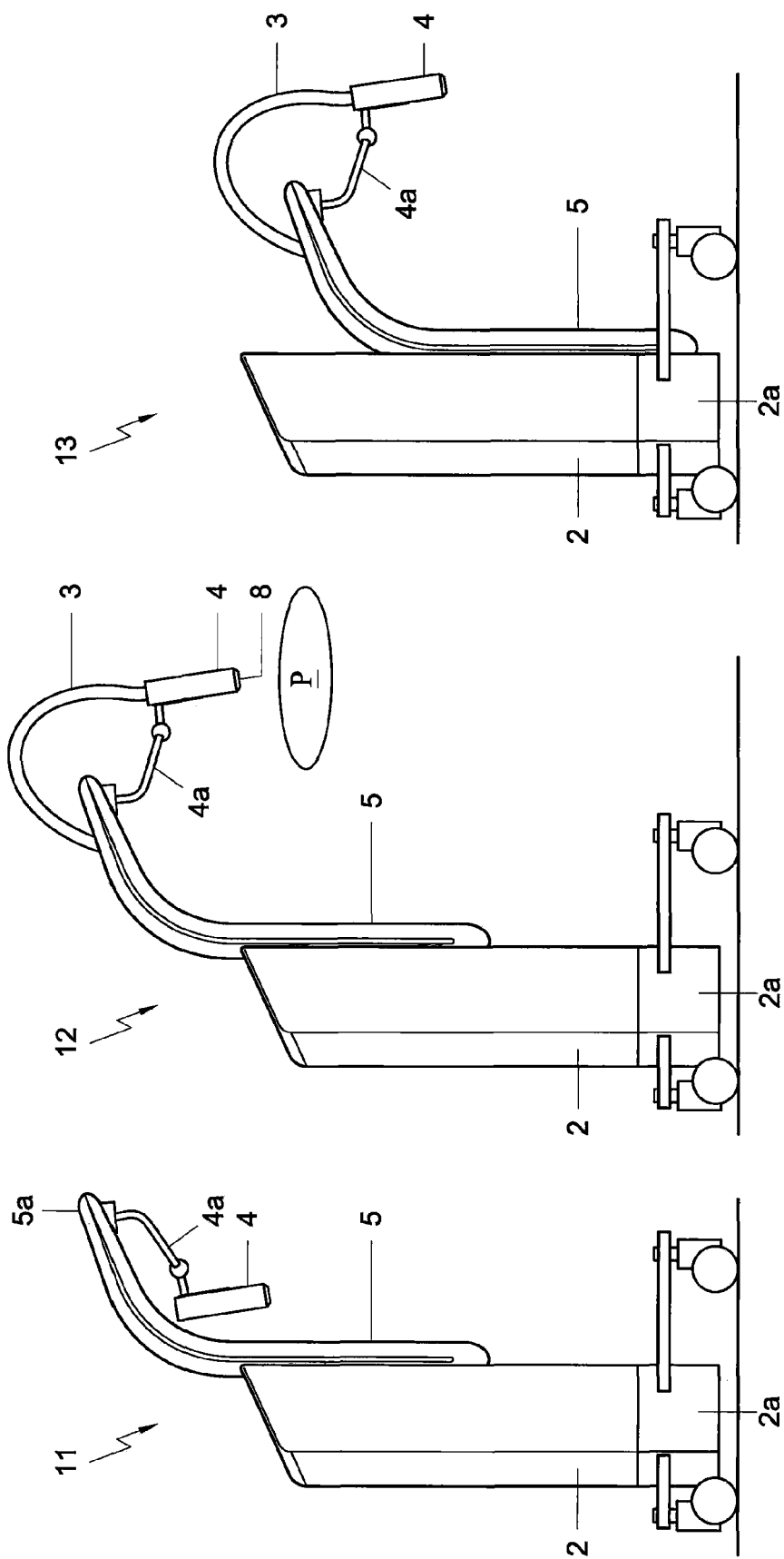
FIG. 1c presents a schematic view of the mobile X-ray unit, illustrating displacement of the X-ray applicator relative to a base of the mobile X-ray unit, according to embodiments of the present disclosure.

FIG. 1c illustrates the displacement of the X-ray applicator 4 of the X-ray unit 10. It will be understood that the mobile X-ray unit 10 may be configured so as to support a broad range of translational and rotational movements of the X-ray applicator 4.

In view 11, the X-ray applicator 4 is in a retracted position. It will be appreciated that cabling is not depicted for clarity reasons. The retracted position may be suitable for transport of the mobile X-ray unit 10 towards a booth and/or for maneuvering the X-ray unit 10 around the patient. In order to retract the X-ray applicator 4 as close as possible to the base 2, the articulated arm 4a may be positioned under the outer portion 5a of the displaceable panel 5. For ensuring stability of the mobile X-ray unit 10 during maneuvering thereof, a load block 2a may be provided for lowering the point of gravity of the X-ray unit 10.

In view 12, the X-ray applicator 4 may be in an extended position (i.e., working position) having an X-ray exit surface 8 oriented towards a patient P. In order to suitably position the X-ray applicator 4 with respect to the patient P, the displaceable panel 5 may be moved to an intermediate position located between the lowest stand position and the highest stand position of the displaceable panel 5. The articulated arm 4a may be used for suitably rotating the X-ray applicator 4 about a rotation axis. In one embodiment, the rotation axis may coincide with a direction in which the X-ray beam is emitted from the exit surface 8 of a vertically oriented X-ray applicator 4.

In view 13, the X-ray applicator 4 may be in a lowered position. For this purpose the displaceable panel 5 may be in its lowest position and the arm 4a may be used for orienting the X-ray applicator 4 in a desirable way.

Figure 2:
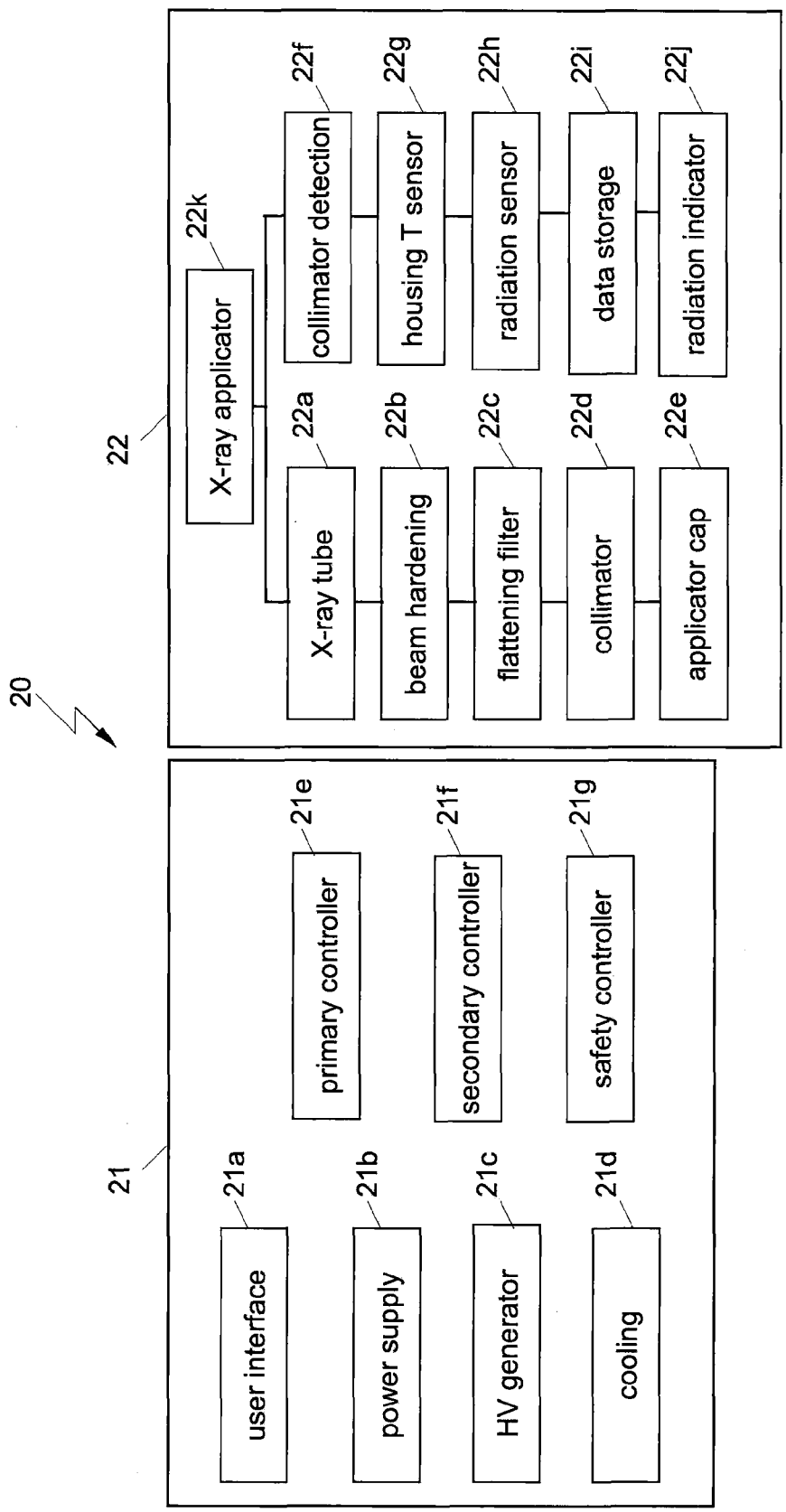
FIG. 2 presents a diagrammatic representation of the mobile X-ray unit, according to embodiments of the present disclosure.

FIG. 2 is a diagrammatic representation of the mobile X-ray unit 10 according embodiments of the present disclosure. The mobile X-ray unit 10 includes a high voltage supply, preferably adapted to generate 50-75 kV X-rays in a suitable X-ray tube, a cooling system for cooling the X-ray tube 22a during use, and a control system 21d for controlling electronic and electric parameters of sub-units of the X-ray unit during use. View 20 diagrammatically depicts main units of the control system 21 and of the X-ray applicator 22.

The control system 21 includes a hard wired user interface 21a for enabling switching on and switching off of the high voltage supply 21b. In some embodiments, the high voltage supply 21b includes a high voltage generator 21c with improved ramp-up and ramp-down characteristics. The high voltage supply is preferably operable for delivering power of about 200 W in use. In some embodiments, the ramp-up time may be of the order of 100 ms. The hard wired interface 21a, may also be arranged to automatically switch on the cooling system 21d when the high voltage generator is switched on. In addition, the control system 21 may include a primary controller 21e arranged for controlling the dose delivery from the X-ray applicator 22 in use. The primary controller 21e may be provided with a primary counter adapted to register time lapsed after the X-ray radiation is initiated. The primary counter may then automatically switch off the high voltage supply to the X-ray tube 22a in the event a pre-determined dose is reached. It will be appreciated that the pre-determined dose is at least dependent on the energy of the X-rays and the dose rate, which may be calibrated in advance. Where calibrated data is made available to the primary controller, adequate primary dose delivery control may be achieved. In some embodiments, a secondary controller 21f may be provided for enabling an independent loop of dose delivery control. The secondary controller 21f may be connected to a dose meter accommodated inside the X-ray applicator 22 in the X-ray field before the collimator 22d. Accordingly, the dose meter may provide real-time data on actual dose delivery taking into account dose variation during ramp up and ramp down of the high voltage source. Still preferably, the control system 21 may include a safety controller 21g adapted to compare readings from the primary controller 21e and the secondary controller 21g for switching off the high voltage generator 21c after a desired dose is delivered. Additionally and/or alternatively, the safety controller 21g may be wired to guard emergency stop, door interlock, and a generator interlock.

The X-ray applicator 22 may include an X-ray tube 22a housed in an outer housing (shielding) 22k. In the exemplary embodiment, a target element, a collimator 22d, and an exit window may be in parallel so that the generated X-ray beam may be propagated substantially parallel the longitudinal axis of the X-ray tube 22a. The X-ray tube 22a may have a target element-collimator distance of between 4 and 10 cm, and preferably 5 and 6 cm. The X-ray applicator 22 may further include a beam hardening filter 22b selected to intercept low-energy radiation and a beam flattening filter 22c, designed to intercept portions of X-ray radiation for generating a substantially flat beam profile near the exit surface of the X-ray applicator 22. Further, the X-ray applicator 22 may comprise one or more collimators 22d arranged to define treatment beam geometry. In some embodiments, a set of collimators 22d may be used having, for example, diameters of 1, 1.5, 2, 2.5, 3, 3.5, 4, 4.5, and 5 cm. It will be appreciated that although circular collimators are discussed, collimators of any shape, such as square, elliptic or custom made collimators are possible. It may be advantageous to have an X-ray applicator 22 with automatic collimator detection device 22f adapted to automatically signal which collimator is being used. In some embodiments, resistive sensing may be used to identify which collimator 22d is being used. In particular, each collimator may be provided with at least a couple of projections for bridging a resistive path provided in a collimator receptacle. The resulting electrical resistance of the receptacle constitutes a signal representative of a collimator being used.

The X-ray applicator 22 may also include a built-in temperature sensor 22g adapted to signal temperature of the X-ray tube 22a and/or its shielding 22k. The signal from the temperature sensor 22g may be received by the control system 21 which may carry out the analysis thereof. Should the measured temperature be elevated beyond an allowable level, an alarm signal may be generated. Optionally, a shut-off signal to the high voltage generator may be provided. The X-ray applicator 22 may further include a radiation sensor 22h arranged inside the outer housing 22k for detecting X-ray radiation which may be delivered by the X-ray tube 22a. Preferably, for safety reasons, the X-ray applicator 22 may include a non-volatile data storage 22i arranged for recording operational parameters at least of the X-ray tube 22a. Further, to enhance radiation safety, the X-ray applicator 22 may be provided with a radiation indicator 22j arranged for providing a visual and/or an audio output to the user and/or the patient regarding ON/OFF condition of the X-ray tube 22a. It will be appreciated that the radiation indicator 22j may include a plurality of signaling devices. In one embodiment, at least one signaling device, for example a light emitting diode (LED), is associated with the X-ray applicator 22 and provided on the X-ray applicator 22. It is understood, however, that the signaling devices may be positioned at any other location on the mobile X-ray unit.

Figure 3:
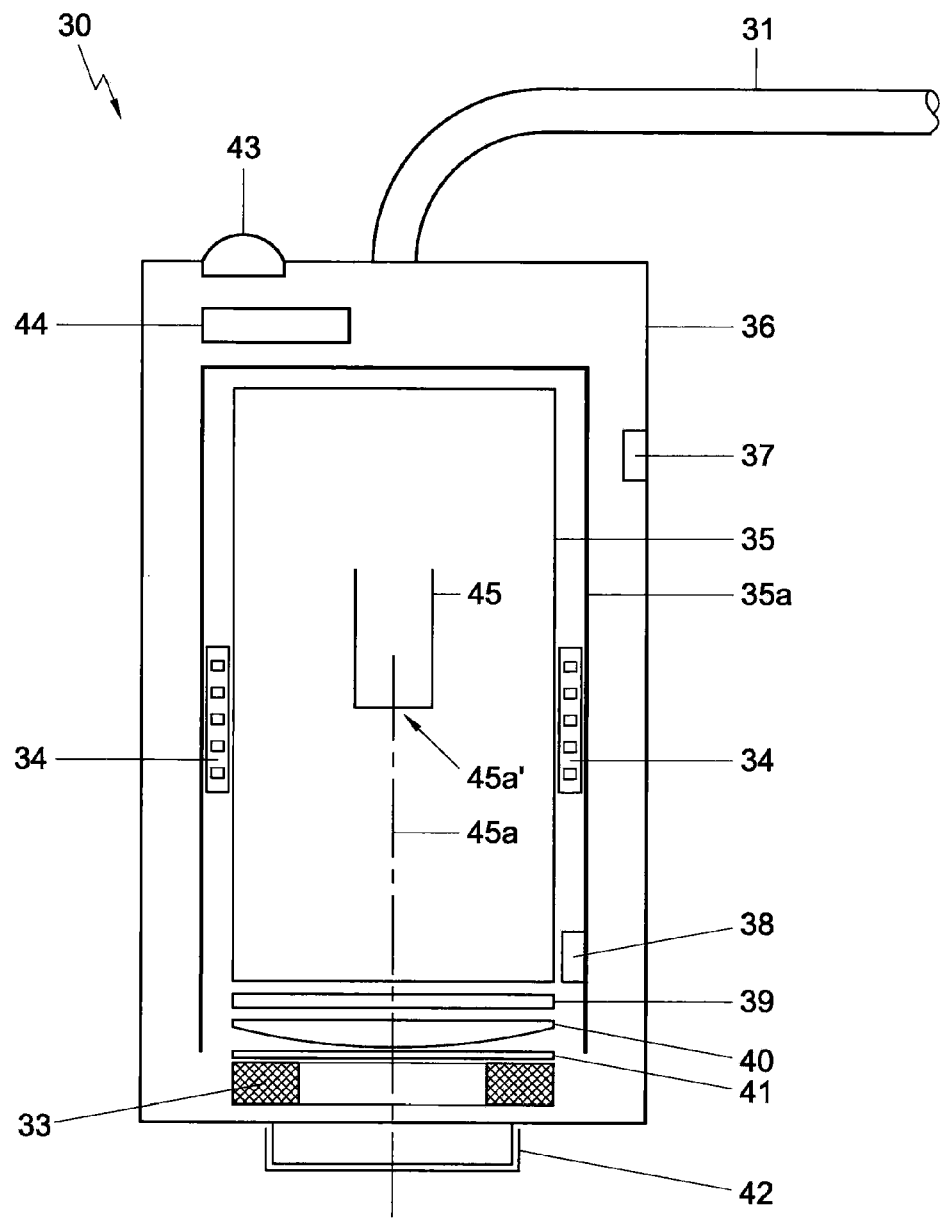
FIG. 3 presents a cross-sectional view of an X-ray applicator of the mobile X-ray unit, according to embodiments of the present disclosure.

FIG. 3 presents a cross section of an X-ray applicator of the mobile X-ray unit. The X-ray applicator 30 comprises an outer housing 36 accommodating the X-ray tube 35 provided with external shielding 35a. The X-ray tube 35 includes an anode 45 arranged to emit a beam of X-rays having a longitudinal propagation axis 45a. In accordance with one aspect of the present disclosure, the anode 45 may be arranged so that its longitudinal axis 45a is substantially parallel with a longitudinal axis of the X-ray tube 35 so that the X-ray beam propagates along a longitudinal axis of the X-ray tube 35.

In some embodiments the distance between the target element (disposed on an outer surface of an anode) and the collimator 33 may be in the range between 4 and 10 cm, and preferably 5 and 6 cm. Such a relatively short target element-collimator distance may generate an X-ray beam having a substantially narrow penumbra (1.5-1.8 mm for 20/80% lines) and good beam flatness. It will be appreciated that the distance between the anode and the collimator may be a distance between the target element plate 45a' and a midplane of the collimator 33. The X-ray applicator 30 may further include a filter 39 for hardening the X-ray beam emanating from the target element 45, a beam flattening filter 40 for flattening out a beam profile, and collimator 33 insertable in a collimator receptacle 41.

A cooling system 34 may be provided so as to prevent overheating of the X-ray tube 35. In one embodiment, the cooling system 34 may be arranged in the space between the X-ray tube 35 and the shielding 35*a* in contact with the surface of the X-ray tube 35. A suitable coolant may be provided using a pipe 31. It is contemplated that the coolant may be water, a pressurized gas, or even a special oil. The X-ray applicator 30 may further comprise a temperature sensor 37.

The X-ray assembly 30 may further include a suitable radiation detector 38 connected to a radiation indicator 43. Data collected by the radiation detector 38 may be stored in a data storage unit 44.

In order to protect an X-ray exit surface of the X-ray applicator 30 from intra-patient contamination, an applicator cap 42 may be provided to cover at least the exit surface of the X-ray applicator 30. In some embodiments, the applicator cap 42 is thick enough to fully intercept secondary electrons emanating from the X-ray applicator.

Figure 4:
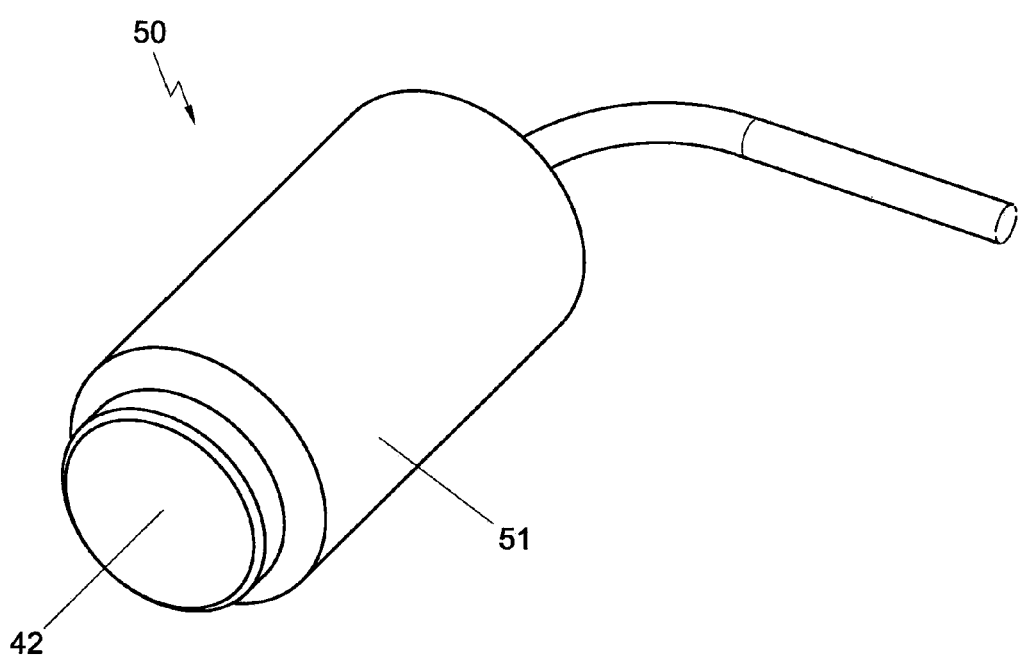
FIG. 4 presents a partial perspective view of the X-ray applicator of FIG. 3 provided with an applicator cap, according to embodiments of the present disclosure.

FIG. 4 presents a partial perspective view of the X-ray applicator of FIG. 3 with an applicator cap. The applicator cap 32 may be manufactured from PVDF (polyvinylidene fluoride) and may have a thickness of 0.4-0.7 mm, and preferably 0.6 mm, across the window portion. The applicator cap may have density of about 175-1.8, and preferably 1.78. Alternatively the applicator cap 42 may have a thickness of about 0.3-0.6 mm, and preferably 0.5 mm, across the window portion. In those embodiments, the applicator cap 32 may have a density of 1.30-1.45, and preferably 1.39. Further, the applicator cap 42 may be manufactured from PPSU (polyphenylsulfone). These materials may be particularly suitable as they as stable under influence of the X-rays and are suitable for different types of sterilization procedures, such as chemical sterilization, or sterilization under elevated temperatures.

Applicator cap 42 may be substantially transparent to X-rays, and may be manufactured from glass, plastic, or ceramic materials. In some embodiments, applicator cap 32 may also be manufactured from a metal. In the latter case, the applicator cap 42 may be sterilized, otherwise, the applicator cap 42 may be a disposable applicator cap. In view 50 of FIG. 4, it is seen that the outer dimension of the X-ray applicator 51 may be larger than the outer dimension of the exit portion covered by the applicator cap 42. Although such embodiment is preferable for minimizing total weight of the X-ray applicator 51, it is possible that the exit portion has the same dimension as the body of the X-ray applicator 51.

Figure 5:
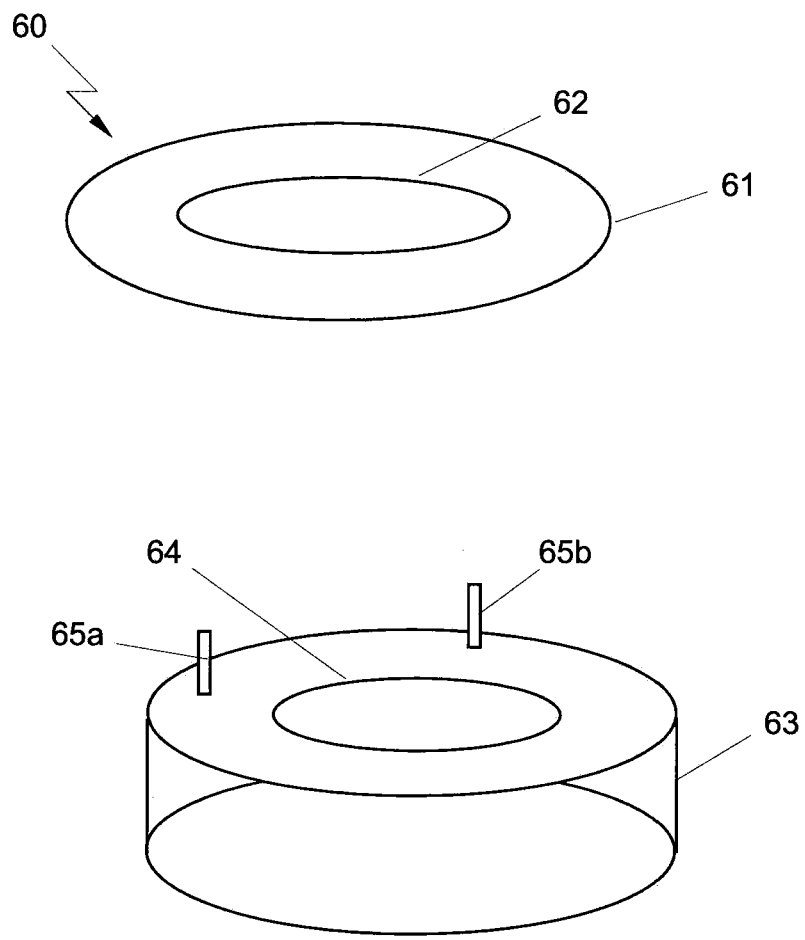
FIG. 5 presents a perspective view of a collimator provided with identification devices and a collimator receptacle, according to embodiments of the present disclosure.

FIG. 5 presents a perspective view of a collimator with identification devices. The collimator 63 may be provided with a central opening 64 for defining a shape and dimension of the resulting X-ray beam emitted from the X-ray applicator 30 as is discussed with reference to FIG. 3. The collimator 63 may be adapted to be received in a collimator receptacle 61, which may be shaped as a suitable chamber where the collimator 63 is to be firmly fitted. In order to enable automatic collimator identification, the collimator may be provided with two projections 65*a*, 65*b*, configured to interact with a resistive path 62 in the collimator receptacle 61. When the projections 65*a*, 65*b* come into contact with the path 62 a net resistance of the collimator receptacle may be changed. The change in the resistance of the collimator receptacle 61 may be used to indicate when the collimator has been inserted in the collimator receptacle 61. It will be appreciated that for a set of collimators, each collimator may be provided with a unique pair of projections leading to a distinguishable change in the net resistivity of the collimator receptacle 61. Those skilled in the art will readily appreciate that a plurality of pairs 65*a*, 65*b* may be positioned at different locations on a surface of the collimator 63. Alternatively, it is possible to provide each collimator 63 with an electronic identification device such as, for example, a chip cooperating with a plug. When the plug is plugged-in the collimator receptacle 61 (provided with a cooperating socket), a signal may be transferred to the control unit of the mobile X-ray unit.

Figure 6:
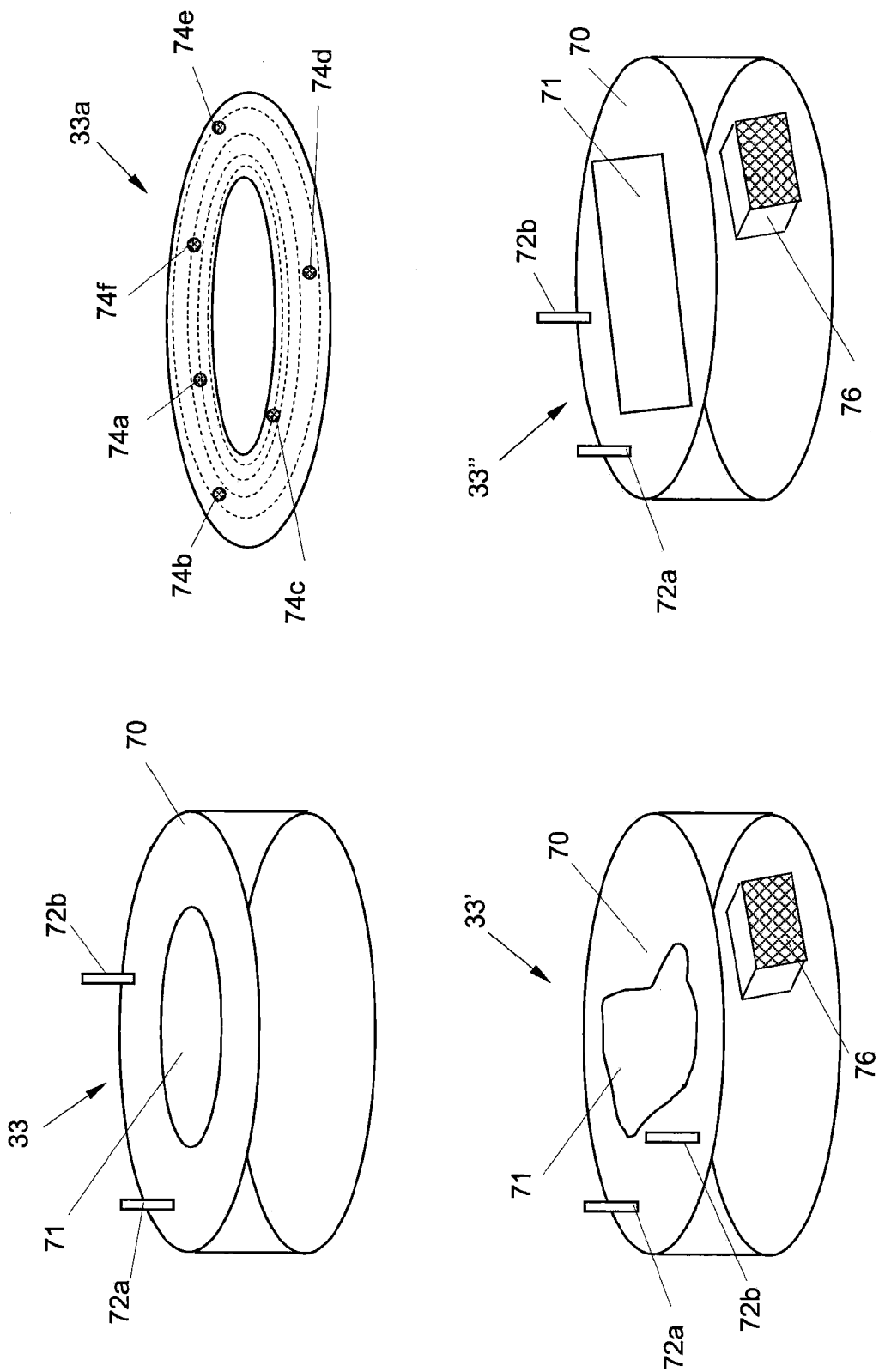
FIG. 6 presents a perspective view of an alternative collimator and alternate collimator receptacle, according to embodiments of the present disclosure.

FIG. 6 presents an alternative embodiment of a collimator 33 having identification devices. Different embodiments of a collimator 33, shown in FIG. 3, will be discussed here in more detail. The collimator 33 may be provided with an aperture 71, which may have any shape. The identification devices 72*a*, 72*b*, may be used for automatically detecting whether a correct (i.e. intended) collimator is being inserted in the X-ray applicator 30. For example, the identification device 72*a*, 72*b* may be spring loaded pins arranged for interacting with a resistive body (shown in the view 33*a*) for causing a change in a net resistance of the resistive body. By detecting a signal representative of the absolute or relative resistance of the resistive body, a control unit may identify when a collimator 33 is within a collimator receptacle.

In view 33*a*, a schematic embodiment of the resistive body is depicted, wherein each pad of the series 74*a*, 74*b*, 74*c*, 74*d*, 74*e*, 74*f* is attributed to a separate resistive contact circle (only few are shown for clarity). The net resistive change of the resistive path 33*a* depends upon where the pin 72*a* or 72*b* contacts a resistive circle of the resistive circuit 33*a* and will change according to the contact positions. The individual collimators of the type 33*a*, may be coded by positioning the contact pins 72*a*, 72*b* at different locations on the outer surface 70.

In alternative embodiments 33' and 33", the contact pins 72*a*, 72*b* may be supplemented by a contact bar 76, used for locking and/or enabling an appropriate insertion of the collimator 33 into a collimator receptacle. This feature is particularly advantageous for collimators 33" not having rotational symmetry. In a still further embodiment, the collimators and/or the pins may be color coded.

When installed on the X-ray applicator 30, the pins of the collimator may contact pads on X-ray applicator 30. This receiving portion of the X-ray applicator 30 may have flat region with a plurality of contact pads arranged around the lower base portion of the X-ray applicator 30. Thus, when the collimator is placed in the collimator receiving receptacle and secured in place, one of the contact pads will engage with a corresponding contact pin on the X-ray applicator 30. Each collimator will have a specific arrangement of contact pins engaging with a specific pair of pads on the X-ray applicator 30. Each of the pins can be connected to the control unit in the base 2 in such a manner as to complete a specific and different electric circuit to identify the collimator and transmit a specific signal to the display panel 7. This method has the advantage that contacts need only be established between the pads and contact pins, no actual measurement of resistance (or conductivity) needs to be made. This is advantageous because minimal attention needs to be given to dirty or soiled contacts, a slight deterioration of which could affect the reading and so lead to an incorrect treatment being administered. It is contemplated that a variety of contact pins and pads can be provided. In this way, collimators with different specifications can be uniquely identified.

Alternatively, it may be possible to provide each collimator with electronic identification device such as, for example, a chip cooperating with a plug. When the plug is plugged-in the collimator receptacle (provided with a cooperating socket) a signal may be communicated to the control unit of the mobile X-ray unit.

Figure 7:
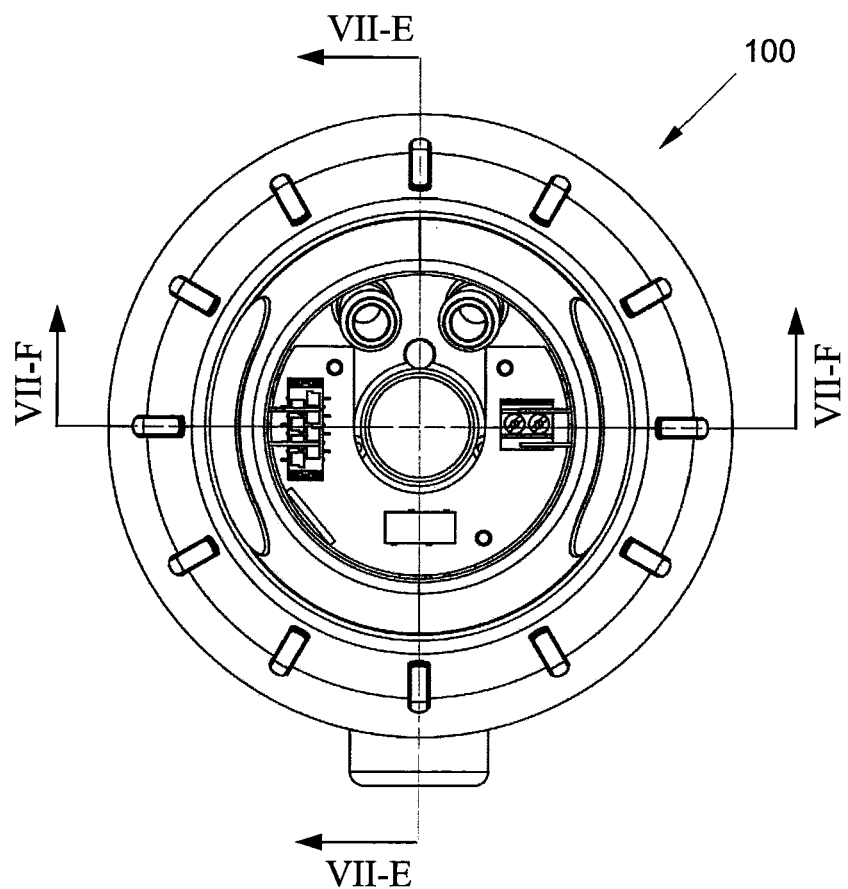
FIG. 7 presents an end view of the X-ray tube, according to embodiments of the present disclosure.

FIGS. 7, 7E-E, and 7F-F, illustrate various views of the X-ray tube. The X-ray tube 100 has a body 102 enclosing at one end a window 104 through which the X-rays pass. See FIG. 7 cross-section E-E. The exit window 104 is made from a thin sheet of Beryllium metal. An applicator cap 106 may be positioned over the exit window 104 so as to covering the exit window 104 and protect exit window 104. Applicator cap 106 may be made from a plastic material. The applicator cap may be manufactured from PVDF (polyvinylidene fluoride) and may have a thickness of about 0.4-0.7 mm, and preferably 0.6 mm, across the window portion. Alternatively, the applicator cap 106 may be manufactured from PPSU (polyphenylsulfone) and may have a thickness of about 0.3-0.6 mm, and preferably 0.5 mm, across the window portion. Alternate metals may also be suitable.

In the tube body 102 a target element 108 is located at a range between 4 and 10 cm from the collimator 130, and preferably between 4 and 5 cm from the collimator 130 (see FIG. 7, cross-section F-F). It will be appreciated that this distance is measured between the outer surface of the target element 108 and a midplane of the collimator 130. The target element 108 may be made from Tungsten metal to provide the desired X-ray spectrum. The tungsten tip of the target element 108 may be mounted on a large anode assembly 110 which also serves to conduct away the heat created from the generation of the X-rays in the target element 108. Most of the anode assembly 110 may be made from copper. The cathode 112 (see FIG. 7, cross-section F-F) may be located slightly off-axis near the end window 104. Electrons emitted from the cathode may be accelerated across the gap by the potential difference between the cathode and anode, in this case set at about 70 kV, to the target element 108 where the impact causes the generation of X-rays in a known manner. X-rays emitted from the target element 108 pass through a beam hardening filter 122 before passing through a collimator 130 and an exit surface 124 on the applicator cap 106. The collimator 130 may be housed in a suitable collimator receptacle 128.

The anode assembly 110 may be mounted in the body 102 and electrically insulated. One of a number of known techniques and materials can be used to provide the desired level of insulation between the anode assembly 110 and the body 102.

As is well known in the art, the production of X-rays generate a large amount of heat. Accordingly, it may be necessary to cool the tube in order to maintain it at a safe temperature. Various cooling mechanisms are known and used in the art. In one embodiment, the X-ray tube 100 is cooled by cooled water forced around the anode region. Cooled water enters the back of the tube by a first conduit 116 and leaves by a second conduit 118 (see FIG. 7, cross-section F-F). The water cooling circuit is a closed loop circuit, with the water leaving the tube assembly 105 to be cooled by a remote cooler (not shown) before returning to the X-ray tube 100. It is contemplated that oil or another liquid may be used as the cooling medium. It is also known that a pressurized gas may be used as an effective coolant in some applications.

As is known in the art, X-rays are generated and emitted in all directions, however the body 102 of the X-ray tube 100 and other internal components will tend to reduce the amount of radiation emitted from the body 102 of the X-ray tube 100 to a minimum, with most of the radiation emitted from the exit window 104. The thickness of the shielding provided by the body 102 may be designed so that it provides at least the minimum level of shielding required for safe use by the operator.

A high voltage cable assembly 120 is connected to the anode assembly 110. The high voltage cable assembly 120 may be connected to flexible cable means (not shown) which in turn may be connected to a high voltage power supply.

A radiation detector 114 (see FIG. 7, cross-section F-F) may be placed outside the path of the X-ray beam emitted from the target element 108 and passing through the exit window 104. This detector 114 may be any known radiation detector. In one embodiment, the radiation detector may be a hardened semi-conductor connected to an amplifier. The radiation detector 114 may detect when the tube 102 is working and emitting X-ray energy. Output from the detector 114 may connected to a control unit, and the output signals from the detector 114 may be used to provide an optical indication to a user of whether the tube is operating or not. In this manner, X-ray detector 114 may used to detect if the X-ray tube is on or off.

With further calibration of the radiation detector 114, it may be possible to determine and calculate the X-ray dose administered to the patient during the treatment. In this manner, it may be possible to have a real time dosimetry measurement system, in which the precise amount of radiation dose administered can be determined. Once the dose rate is known, a treatment plan can be modified during treatment. This may be advantageous because it may enable a very accurate and carefully controlled dose of X-rays to be administered.

In order to enable the X-ray tube 100 to be placed accurately over a tumour, a tumour illumination device may be is used. The tumour illumination device may include a plurality of lights 126 placed around the circumference of the X-ray tube 100 near the end window 104. When in use, the lights shine onto the skin of the patient. Since the lights 126 are positioned around the circumference of the tube body 102, at a short distance from the end of the X-ray tube 100 they create a circle of light with a sharp cut off of the inner part of the circle. In this way, the position of the lights on the tube body 102 may create a shadow. This shadow circle may be used to indicate the region which will be subject to irradiation when the X-ray tube 100 is turned on. It should be appreciated the area within the circle may not be completely dark; the ambient light may be able to enter the shadow region.

In some embodiments, the lights 126 are white LEDs which can be bright enough to clearly illuminate the target region but do not generate amounts of heat and have very long lives. The lack of heat generation is important because the lights will be in close proximity to the skin of the patient, and so it is important to minimise the risk of burning or other damage to the skin. Other colours of LEDs may be used. Alternatively, other light sources could be used, such as known filament lamps or even a remote light source connected to the ring by fibre optic cables.

Figure 8:
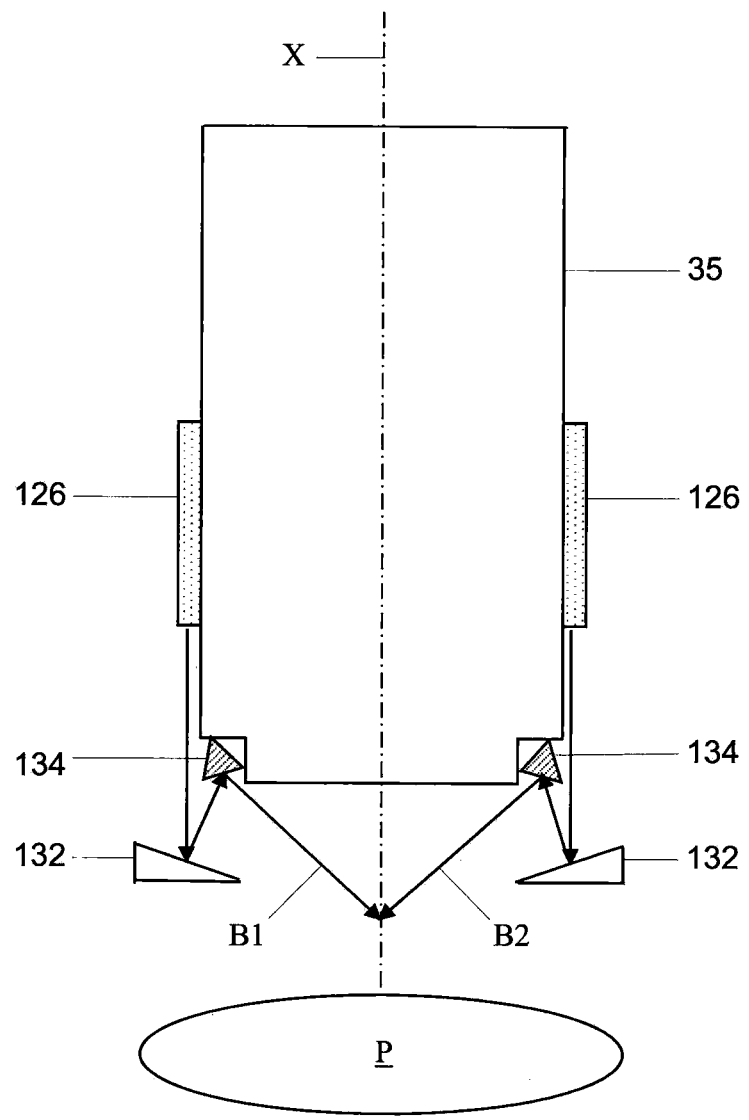
FIG. 8 presents a schematic view the X-ray tube, according to embodiments of the present disclosure.

FIG. 8 presents a schematic view of the indicator, in accordance with an embodiment of the present disclosure. In this embodiment, an indicator (e.g., a light source 126) may be provided at a side surface of the X-ray tube 35. The light source 126 may be an LED or any other suitable light source. Light emitted from the light source 126 may impinge on a reflective surface of the X-ray collimator 132. The light beam may then be reflected from a further reflective surface 134 and directed as respective beams B1 and B2 towards the central axis X of the X-ray tube 35. It will be appreciated that the X-ray tube 35 may be suitably shaped and manufactured for providing a reflective body 134. The reflective body 134 may be a concentric reflective ring attached in a corresponding recess of the X-ray tube 35. It will be further appreciated that the reflective surfaces 132 may be advantageously provided on a collimator surface facing away from the patient towards the X-ray source (not shown), positioned on the axis X. Those skilled in the art will readily appreciate how to arrange the collimator 134, and the X-ray tube 135, shown in FIG. 3 for enabling the geometry discussed in FIG. 6. A light spot generated by the light source 126 in the manner described above may be used for accurately positioning the X-ray tube 35 with respect to the patient P.

It will be further appreciated that the reflective surfaces 132 may be advantageously provided on a collimator surface facing away from the patient towards the X-ray source (not shown), positioned on the axis X. Those skilled in the art will readily appreciate how to arrange the collimator, and the X-ray tube, shown in FIG. 3 for enabling the geometry discussed in FIG. 6.

A light spot generated by the indicators 126 in the manner described above may be used for accurately positioning the X-ray tube 35 with respect to the patient P.

It will be further appreciated that the spatial position of the intersection between the beams B1 and B2 may be chosen to provide a minimum spot at a pre-determined distance from an outer surface of the X-ray applicator (not shown) accommodating the X-ray tube 35. For example, the pre-determined distance may be selected at 1, 2, 3, 4, and 5 cm from the outer surface of the X-ray applicator. In this way, the region of interest on the patient P and the central axis of the X-ray beam may be aligned and maintained. It may be advantageous to select the pre-determined distance at about 2-3 cm from the outer surface of the X-ray applicator for enabling maneuverability of the X-ray applicator without having risk of contacting the patient. When the X-ray applicator is set with respect to the patient P, using the articulated arm 4a, shown in FIG. 1a and the indicator (i.e., light source 126), it may be further positioned using suitable fine mechanics.

It will be further appreciated that while the indicator (i.e., light source 126) and the reflective bodies are explained with reference to the X-ray tube 35, it may be possible to implement a similar configuration attaching the indicators to an outer surface of the X-ray applicator 4, depicted in FIG. 1. In this case instead of using collimators for implementing a reflective purpose, a dedicated reflector may be used.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile X-ray unit comprising:
a base for accommodating a control unit for controlling an X-ray treatment applicator and a power supply for supplying power to the X-ray treatment applicator;
an articulated arm associated with the base and coupled to the X-ray treatment applicator, the X-ray treatment applicator having an X-ray tube including an anode for generating an acceleration field and a target element for generating an X-ray beam, wherein a longitudinal axis of the anode is substantially parallel to a longitudinal axis of the X-ray tube.

2. The mobile X-ray unit according to claim 1, wherein the X-ray treatment applicator includes a longitudinal axis, the longitudinal axis of the X-ray tube being substantially parallel to the longitudinal axis of the X-ray treatment applicator.

3. The mobile X-ray unit according to claim 2, wherein the longitudinal axis of the anode, the longitudinal axis of the X-ray tube, and the longitudinal axis of the X-ray treatment applicator are co-axially disposed.

4. The mobile X-ray unit according to claim 1, wherein the anode includes an exit window for emitting the X-rays generated at the target element, the X-ray tube further including a collimator for shaping the generated X-ray beam, wherein the target element, the exit window, and the collimator are axially arranged in a spaced apart configuration.

5. The mobile X-ray unit according to claim 4, wherein a distance between the target element and the collimator is in the range between 4 and 10 cm.

6. The mobile X-ray unit according to claim 5, wherein a distance between the target element and the collimator is in the range between 5 and 6 cm.

7. The mobile X-ray unit according to claim 4, wherein the collimator includes identification devices configured to generate a signal in the control unit representative of collimator characteristics.

8. The mobile X-ray unit according to claim 7, wherein the collimator is configured to be received in a receptacle having a resistive path, the collimator having a set of projections configured to cooperate with the resistive path of the receptacle to generate the signal.

9. The mobile X-ray unit according to claim 4, further including a set of collimators each having unique identification devices configured to generate a signal and identify the collimator.

10. The mobile X-ray unit according to claim 9, wherein each collimator has at least one contact for contacting at least one of a plurality of contact pads on the X-ray treatment applicator for generating the signal.

11. A method for manufacturing a mobile X-ray unit, the method comprising:
assembling the X-ray unit including a base for accommodating a control unit for controlling an X-ray treatment applicator and a power supply for supplying power to the X-ray treatment applicator, wherein the X-ray unit includes an articulated arm associated with the base and coupled to the X-ray treatment applicator, the X-ray treatment applicator having an X-ray tube including an anode and a target element;
connecting the X-ray treatment applicator to the base by a connector; and
arranging the X-ray tube so that a longitudinal axis of the anode is disposed substantially parallel to a longitudinal axis of the X-ray tube.

12. The method according to claim 11, wherein the X-ray tube includes an exit window and a collimator for shaping the X-ray beam.

13. The method according to claim 12, wherein the method further includes the step of arranging the target element, the exit window, and the collimator to be substantially aligned on the longitudinal axis of the X-ray tube in a spaced apart configuration.

14. The method according to claim 13, wherein a distance between the target element and the collimator is in a range between 4 and 10 cm.

15. The method according to claim 11, the method further including aligning the longitudinal axis of the anode, the longitudinal axis of the X-ray tube, and a longitudinal axis of the X-ray treatment applicator.

16. A method of delivering an X-ray beam for irradiating a superficial lesion using an X-ray unit, the method comprising:
positioning the X-ray unit relative to the superficial lesion, the X-ray unit including a base for accommodating a control unit for controlling an X-ray treatment applicator and a power supply for providing power to the X-ray treatment applicator, an articulated arm associated with the X-ray treatment applicator, the X-ray treatment applicator having an X-ray tube including an anode and a target element;

generating an acceleration field at the anode; and generating an X-ray beam at the anode, wherein a longitudinal axis of the anode is substantially parallel to a longitudinal axis of the X-ray tube.

* * * * *